United States Patent
Stephenson et al.

(10) Patent No.: US 6,984,376 B2
(45) Date of Patent: Jan. 10, 2006

(54) METHODS OF INHIBITING DENTAL EROSION/DISCOLORATION USING A BEVERAGE COMPOSITION COMPRISING A LONG CHAIN POLYPHOSPHATE

(75) Inventors: Gary Stephenson, Newcastle-upon Tyne (GB); Dale Alan Cooper, Mason, OH (US); Robert Vincent Faller, Loveland, OH (US); Arif Ali Baig, Mason, OH (US)

(73) Assignee: Procter & Gamble, Cincinnati, OH (US)

( * ) Notice: Subject to any disclaimer, the term of this patent is extended or adjusted under 35 U.S.C. 154(b) by 241 days.

(21) Appl. No.: 10/318,963

(22) Filed: Dec. 13, 2002

(65) Prior Publication Data

US 2003/0138384 A1 Jul. 24, 2003

Related U.S. Application Data

(63) Continuation-in-part of application No. 09/489,310, filed on Jan. 21, 2000.

(51) Int. Cl.
*A61K 7/16* (2006.01)
*A61K 7/20* (2006.01)

(52) U.S. Cl. .................. 424/49; 424/57; 426/548; 426/590

(58) Field of Classification Search ............. 424/49–88; 426/548, 590
See application file for complete search history.

(56) References Cited

U.S. PATENT DOCUMENTS

| | | | | |
|---|---|---|---|---|
| 4,143,172 A | * | 3/1979 | Mitchell et al. | 426/532 |
| 4,163,069 A | * | 7/1979 | Melachouris et al. | 426/582 |
| 4,255,414 A | | 3/1981 | Lembke et al. | |
| 4,349,533 A | | 9/1982 | Dent et al. | |
| 4,885,155 A | | 12/1989 | Parrar, Jr. et al. | |
| 4,935,225 A | | 6/1990 | Curtis et al. | |
| 4,943,443 A | * | 7/1990 | Evers | 426/592 |
| 4,980,182 A | * | 12/1990 | Kwon et al. | 426/130 |
| 5,017,362 A | | 5/1991 | Gaffar et al. | |
| 5,064,640 A | | 11/1991 | Kleber et al. | |
| 5,094,870 A | | 3/1992 | Scaglione et al. | |
| 5,654,027 A | * | 8/1997 | Chalupa | 426/573 |
| 5,827,505 A | | 10/1998 | Hughes et al. | |
| 5,833,957 A | | 11/1998 | Winston et al. | |
| 5,866,102 A | | 2/1999 | Winston et al. | |
| 5,885,553 A | | 3/1999 | Michael | |
| 5,939,052 A | | 8/1999 | White, et al. | |
| 6,106,883 A | * | 8/2000 | Sokolik et al. | 426/573 |
| 6,440,482 B1 | * | 8/2002 | Henson et al. | 426/590 |
| 6,468,576 B1 | * | 10/2002 | Sher et al. | 426/565 |
| 2002/0102220 A1 | * | 8/2002 | Stephenson | |

FOREIGN PATENT DOCUMENTS

| | | | |
|---|---|---|---|
| JP | 04139120 | | 5/1992 |
| WO | WO 96/26648 | | 9/1996 |
| WO | WO 99/21432 | | 5/1999 |
| WO | 01/52796 | * | 7/2001 |
| WO | 01/72144 | * | 10/2001 |
| ZA | 6904743 | * | 1/1970 |

OTHER PUBLICATIONS

McDonald et al., J. Dent. Res. 52(2): 211–216, 1973.*
Reussner et al., J. Dent. Res. 54(2): 365–370, 1975.*
Lussi et al., Caries Res. 29: 349–354, 1995.*
Rugg–Gunn et al., Caries Res. 32: 337–343, 1998.*
McGaughey, Caries Res. 17: 229–271, 1983.*
McGaughey, J. Dent Res. 56(6): 579–587, 1977.*
Larsen, Scand. J. Dent. Res. 83: 13–17, 1975.*
Shibata et al., Arch. Oral. Biol. 27: 809–816, 1982.*
Stadtler, Muller–Brucksscwaiger, Schafer, Huntington, *The Effect Of Sodium Trimetaphosphate On Caries: A 3–year Clinical Toothpaste Trial*, Caries Research, 1996; 30, pp. 418–422.
Larsen, *Degrees Of Saturation With Respect To Agalites In Fruit Juices And Acidic Drinks*, Scandinavia Journal Of Dentistry Research, 1975; 83, pp. 13–17.
Roberts, *Role Of Models In Assessing New Agents For Caries-Prevention –Non-Fluoride Systems*, Adv. Dent. Res. 9(3):304–311, Nov., 1995.
Ingram, Edgar, *Interactions Of Fluoride And Non-Fluoride Agents With The Caries Process*, Adv. Den. Res. 8(2):158–165, Jul. 1994.

(Continued)

*Primary Examiner*—Frederick F. Krass
(74) *Attorney, Agent, or Firm*—S. Robert Chuey

(57) ABSTRACT

The present invention is directed to a method of treating dental erosion, preventing dental discoloration or both comprising orally administering to a mammal (preferably, a human) a beverage composition having a pH of greater than about 5.5; wherein the beverage composition comprises a compound having the structure:

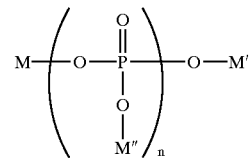

wherein n is an integer averaging from about 7 to about 100 and M, M', and M" are each, independently, selected from the group consisting of sodium and potassium. The present invention is further directed to kits comprising the foregoing beverage composition and information that use of the beverage composition provides treatment against dental erosion, dental discoloration or both.

12 Claims, No Drawings

OTHER PUBLICATIONS

Gilmore, *The Effect On Dental Caries–Activity Of Supplementing Diets With Phosphates: A Review*, Journal Of Public Health Dentistry, vol. 29, No. 3–Summer Issue, 1969, pp. 188–207.

McGaughey, Stowell, *Effects Of Polyphosphates On The Solubility And Mineralization Of HA: Relevance To A Rationale For Anticariew Activity*, Journal Of Dentistry Research, vol. 56 No. 6, pp. 579–587, Jun. 1977.

Reussner, Coccodrilli, Jr., Thiessen, Jr., *Effects Of Phosphates In Acid–Containing Beverages On Tooth Erosion*, Journal Of Dentistry Research, vol. 54, No. 2, pp. 365–370, Mar.–Apr., 1975.

Rugg–Gunn, Maguira; Gordon, McCabe, Stephenson, *Comparison Of Erosion Of Dental Enamel By Four Drinks Using An Intra–Oral Appliance*, Caries Research 1998; 32: pp. 337–343.

Shibata, Morioka, *Antibacterial Action Of Condensed Phosphates On The Bacterium Streptococcus Mutans And Experimental Caries In The Hamster*, Archs Oral Biol., vol. 27, pp. 809–818, 1982.

*The Effect Of Phospates In Breakfast Cereals On Dental Caries*, Nutrition Reviews, vol. 25, No. 9, Sep. 1967, pp. 263–265.

Andlaw, Palmer, King, Kneebone, *Caries Preventative Effects Of Toothpastes Containing Monofluorophosphate And Trimetaphosphate: A 3–Year Clinical Trial*. Community Dentistry And Oral Epidemiol, vol. 3, Jun. 183, pp. 143–147.

Clerehugh, Worthington, Clarkson, Davies, *The Effectiveness Of Two Test Dentrifices On Dental Plaque Formation: A 1–Week Clinical Study*, American Journal Of Dentistry, vol. 2, Special Issue, Sep. 1989 pp. 221–224.

Ingram, *Reaction Between Apatite And Monofluorophosphate: Modification By Fluoride And Condensed* Phosphate, Caries Research, 11:30–38 (1977).

Newesely, *The Chemical Behavior Of Calcium Polyphosphates In Enamel And Dentine*, Caries Research, 1:1–14 (1967).

DeShazer, Ursick, *The Presence Of Polyphosphates In Solutions Of Sodium Monofluorophosphate*, Archs Oral Biol., vol. 13, pp. 1163–1165, 1968.

McGaughey, *Binding Of Polyphosphates And Phosphonates To Hydroxyapatite. Subsequent Hydrolysis Phosphate Exchange And Effects On Demineralization, Mineralization And Microcrystal Aggregation*, Caries Research, 17: (1983), pp. 229–241.

Shaw, *Influences Of Sodium, Calcium and Magnesium Trimetaphosphates On Dental Caries Activity In The Rat*, J. Dent Research, 59(3): Mar., 1980, pp. 644–650.

Mor, Rodda, *Histopathology Of Artificial Caries–Like Lesions Produced By Lactate Buffers With Tripolyphosphate And Diphosphonate Additives*, New Zealand Dental Journal 77; Apr., 1981, pp. 57–61.

Hattab, The State Of Fluorides in Toothpastes, J. Dent. 1989; 17: pp. 47–54.

Stephen, Chestnutt, Jacobson, McCall, Chestera, Huntington, Schafer, *The Effect Of NaF And SMFP Toothpastes On Three–Year Caries Increments in Adolescents*, International Dental Journal, (1994); 44, #3, Supplement 1, pp. 287–295.

Mullane, Kavanagh, Ellwood, Chesters, Schafer, Huntington, Jones, *A Three–Year Clinical Trial Of A Combination Of Trimetaphosphate And Sodium Fluoride In Silica Toothpastes*, J. Dent Research 76 (11): 1776–1781, Nov., 1997.

Stookey, McDonald, Jr., *Influence Of Combinations Of Oat Hulls And Sodium Trimetaphosphate Upon Dental Caries In The Rat*, J. Dent Research 59(5): 838–843, May 1980.

Borggreven, Hoeks, Driessens, Zwanenburg, *The influence Of Various Amphiphilic Phosphates On in Vitro Caries Lesion Formation in Human Dental Enamel*, Caries Research 1992; 26: pp. 84–88.

Lussi, Jaeggi, Jaeggi–Scharer, *Prediction Of The Erosive Potential Of Some Beverages*, Caries Research, 1995, 29: pp. 349–354.

XP–001005462–Robert S. Harris, Abraham E. Nizel, and Norma B. Walsh "The Effect of Phosphate Structure on Dental Caries Development in Rats"; J. dent. Res. Jan.–Feb. 1967, vol. 46 No. 1.

\* cited by examiner

METHODS OF INHIBITING DENTAL EROSION/DISCOLORATION USING A BEVERAGE COMPOSITION COMPRISING A LONG CHAIN POLYPHOSPHATE

RELATED APPLICATIONS

This case is a continuation-in-part of application Ser. No. 09/489,310, filed on behalf of Gary Stephenson, on Jan. 21, 2000.

FIELD OF THE INVENTION

The present invention is directed to methods of treating dental erosion, preventing dental discoloration or both comprising orally administering a beverage composition to a mammal, preferably a human. The beverage composition is preferably not acidic, that is, the pH is above about 5.5. The present invention is further directed to kits comprising the beverage compositions.

BACKGROUND OF THE INVENTION

Beverage compositions, for example, soft drink beverages (e.g., cola beverages) and fruit juice beverages, have the potential when consumed to cause dental erosion and often dental discoloration. Such dental erosion and discoloration can result wherein the beverage composition is acidic in nature, i.e., exhibits a pH of about 5 or below. Additionally, since children are particularly susceptible to dental erosion relative to adults due to the smaller enamel surface to volume ratio, consumption of such beverages may be of particular concern for this group. Accordingly, since many consumers ingest acidic beverage compositions weekly, daily, or even more frequently, it would be advantageous to discover a beverage composition that protects against dental erosion and discoloration.

The art suggests that such factors as pH, fluoride, calcium, and even phosphate concentration may have an effect on dental erosion and/or dental caries. For example, acidic pH, particularly about 5 or below, is typically considered to exacerbate dental erosion (which occurs by direct action of acid on the enamel surface). For example, Lussi et al., "Prediction of the Erosive Potential of Some Beverages", *Caries Research*, Vol. 29, pp. 349–354 (1995) examined the erosive potential of many beverage compositions, all having a pH of less than 5.

Furthermore, Borggreven et al., "The Influence of Various Amphiphilic Phosphates on in vitro Caries Lesion Formation in Human Dental Enamel", *Caries Research*, Vol. 26, pp. 84–88 (1992) suggests enamel softening in the presence of certain polyphosphates at levels below pH 5.5. See Borggreven et al., p. 87.

The art suggests that further factors are important in dental erosion and/or dental caries. Lussi et al. (citation herein above) suggests that fluoride concentration is a further factor contributing to dental erosion. For example, among beverage compositions tested by Lussi et al., the compositions having the highest fluoride concentrations showed the smallest amount of surface softening of the enamel. However, highest phosphate concentrations did not necessarily correlate with decreased surface softening of the enamel. For example, apple juice, having a moderately high phosphate concentration relative to many other beverage compositions tested, was also the most erosive beverage composition tested. See Lussi et al., pp. 352–353.

There has been further experimentation with certain phosphates, including pyrophosphates and polyphospates, with respect to dental health, particularly in the area of dental caries. For example, Städtler et al., "The Effect of Sodium Trimetaphosphate on Caries: A 3-Year Clinical Toothpaste Trial", *Caries Research*, Vol. 30, pp. 418–422 (1996), suggests that trimetaphosphate (a cyclic phosphate) may be effective against dental caries. However, Städtler et al. utilized toothpaste formulations having near-neutral pH rather than a more acidic formulation. Other studies have suggested efficacy against dental caries using certain phosphates in a relatively neutral pH, calcium-containing solution, but the "polyphosphates" studied comprised 2, 3 or 6 phosphates (ortho, trimeta, tripoly, and hexameta phosphates). See e.g., McGaughey et al., "Effects of Polyphosphates on the Solubility and Mineralization of HA. Other studies of the effect of small polyphosphates (P<6) on dental caries include: Relevance to a Rationale for Anticaries Activity", *Journal of Dental Research*, pp, 579–587, June 1977 and Shibata et al., "Antibacterial Action of Condensed Phosphates on the Bacterium Streptococcus Mutans and Experimental Caries in the Hamster", *Archives of Oral Biology*, Vol. 27, pp. 809–816 (1982).

Another study did suggest the efficacy of monocalcium phosphate in low pH powdered beverage compositions for preventing molar erosion. See Reussner et al., "Effects of Phosphates in Acid-Containing Beverages on Tooth Erosion", *Journal of Dental Research*, pp. 365–370, March-April 1975. However, this same study further suggested that beverage compositions supplemented with other phosphates, including sodium hexametaphosphate, did not produce significant protective effects against molar erosion. See Reussner et al., p. 367. These studies generally agree that the tripoly phosphate (P=3) has some benefit for preventing caries. But these studies fail to identify larger polyphosphates that protect teeth from the harmful effects of acidic beverages.

Finally, WO 01/72144 A1, filed by Smithkline Beecham PLC, and claiming priority to a Great Britain application filed on Mar. 27, 2000, discloses the use of longer chain poly phosphates (n=7 to 30) for use in acidic oral compositions (pH between 2.5–5.5) to alleviate tooth damage. This reference, however, does not discuss or contemplate the delivery of higher chain polyphosphates from a non-acidic beverage composition.

Accordingly, there is a continuing need for beverage compositions having a relatively neutral pH, which are effective against dental erosion and discoloration. More specifically, there is a need for beverages that are not acidic enough to attack teeth, but provide protection from the harmful attack of acidic beverages. Moreover, there exists a need for beverages that protect teeth from both erosion and discoloration. These and other benefits are provided by the present invention.

SUMMARY OF THE INVENTION

The present invention is directed to a method of treating dental erosion, preventing dental discoloration or both comprising orally administering to a mammal (preferably, a human) a beverage composition having a pH of greater than about 5.5; wherein the beverage composition comprises a compound having the structure:

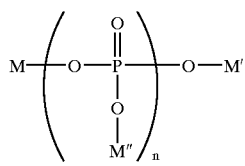

wherein n is an integer averaging from about 7 to about 100 and M, M', and M" are each, independently, selected from the group consisting of sodium and potassium.

The present invention is further directed to kits comprising the foregoing beverage composition and information that use of the beverage composition provides treatment against dental erosion, dental discoloration or both.

It has surprisingly been found that by introducing a relatively long chain poly phosphate to mammalian teeth via a non-acidic beverage that the teeth will be protected from a later attack by an acidic beverage. This protection can last up to four hours and normally exceeds three hours. This is very important because many acidic beverages do not contain ingredients to protect against the damage that such beverages inflict on tooth enamel. As such, it is desirable to provide the protective component through other beverages, for example tap or bottled water. Moreover, because poly phosphate components can bind with calcium and other minerals, it is often undesirable to add the poly phosphates to fortified drinks. Calcium fortified fruit drinks fall within this category, and most of them, orange juice and apple juice for example, are highly acidic. Thus, they will attack the teeth and the addition of poly phosphates to these compositions may be counter productive. That is, the poly phosphates will complex with the fortified minerals, reducing the efficacy of each component. Thus, the ability to introduce a protective composition via a non-acidic beverage, which protects the teeth from attack by an acidic beverage consumed hours later, is a substantial improvement over the art.

The methods and kits of the present invention are described more particularly herein below.

DETAILED DESCRIPTION OF THE INVENTION

The present invention is directed to methods of treating dental erosion and discoloration comprising orally administering a beverage composition to a mammal, preferably a human. The present invention is further directed to kits comprising the beverage compositions and information that use of the beverage composition provides treatment against dental erosion.

Publications and patents are referred to throughout this disclosure. All references cited herein are hereby incorporated by reference.

All percentages and ratios are calculated by weight unless otherwise indicated. All percentages and ratios are calculated based on the total composition unless otherwise indicated.

All component or composition levels are in reference to the active level of that component or composition, and are exclusive of impurities, for example, residual solvents or by-products, which may be present in commercially available sources.

Referred to herein are trade names for components including, but not limited to, certain carbohydrates, flavors, and other components. The inventor herein does not intend to be limited by materials under a certain trade name. Equivalent materials (e.g., those obtained from a different source under a different name or catalog (reference) number) to those referenced by trade name may be substituted and utilized in the compositions, kits, and methods herein.

In the description of the invention various embodiments and/or individual features are disclosed. As will be apparent to the ordinarily skilled practitioner, all combinations of such embodiments and features are possible and can result in preferred executions of the present invention.

The compositions, methods, and kits herein may comprise, consist essentially of, or consist of any of the elements as described herein.

Definitions

As used herein, the term "dental erosion" is defined as loss, softening, and/or demineralization of mammalian tooth substance (i.e., demineralization of enamel of the tooth typically with dissolution of such enamel). Preferably, such loss of tooth substance occurs by direct action of acid on the tooth substance. Such acid may be, for example, present in the oral cavity either naturally, through chronic regurgitation (through conditions such as, for example, anorexia nervosa, bulimia nervosa, and/or gastrointestinal disturbances) and/or through administration of acidic (i.e., having a pH of less than about 5) foods, beverages, pharmaceutical preparations (including over-the-counter and $R_x$), and/or nutraceutical preparations. See e.g., Lussi et al., "Prediction of the Erosive Potential of Some Beverages", *Caries Research,* Vol. 29, pp. 349–354 (1995). Preferably, such chemical processes are not directly related to the action of bacteria (i.e., caries), which more typically results in cavity formation. Dental erosion may result in the aforementioned loss or softening of enamel and demineralization.

As used herein, the term "dental discoloration" is defined as the decrease in whiteness of the tooth enamel, or a darkening, or yellowing of the tooth enamel. Loss of sheen or luster of the tooth enamel is also associated with dental discoloration. Tooth enamel can be measured for discoloration using a standard shade guide, for example, VITA LUMINO® Vacuum Farbskala Shade Guides, a product of VITA Zahnfabrik, of BadSackingen, Germany. The discoloration of tooth enamel can be caused by everyday food and drinks such as coffee, tea, wine, and other beverages with tooth staining potential as well as other sources of potential tooth staining, such as tobacco use (smoked, chewed, etc.), antimicrobial agents, and other compounds known or demonstrated to effect or enhance staining of tooth surfaces, in particular those that deposit stain into the protein film (pellicle) that generally covers all exposed tooth surfaces.

As used herein, the term "treating" with reference to the term "dental erosion" and "dental discoloration" is defined as inhibiting (either partially or completely), reversing, and/or protecting against dental erosion or discoloration with respect to the user of the present beverage composition. Most preferably, the term "treating" with reference to the term "dental erosion" is defined as inhibiting (either partially or completely) and/or protecting against dental erosion or discoloration with respect to the user of the present beverage composition. Wherein dental erosion or discoloration is "treated", conditions such as, for example, softening of enamel, demineralization, darkening, and/or cavity formation may be inhibited, reversed, and/or protected against.

Methods of the Present Invention

The present methods are directed to treating dental erosion, dental discoloration or both comprising orally administering to a mammal a beverage composition having a pH of greater than about 5.5, wherein the beverage composition comprises a polyphosphate compound having the defined structure set forth herein. Surprisingly, it has discovered that, despite the relatively neutral pH of the beverage compositions, the present beverage compositions provide treatment against dental erosion, dental discoloration or both. The inventors herein have further excitingly discovered that such treatment is provided even wherein the beverage composition is substantially free of components which are often associated with treatment of dental erosion, dental discoloration or both, i.e., fluoride and/or calcium. The present inventor has further discovered that such treatment is also provided even wherein the beverage composition is substantially free of phosphate derived from one or more compounds other than the polyphosphate compound defined herein.

In accordance with the methods of the present invention, dental erosion, dental discoloration or both is treated through orally administering to a mammal, preferably a human, a beverage composition having a pH of greater than about 5.5 and comprising the polyphosphate compound as specifically defined herein. As used herein, the term "orally administering" with respect to the mammal (preferably, human) means that the mammal ingests or is directed to ingest (preferably, for the purpose of treatment against dental erosion, dental discoloration or both) one or more beverage compositions of the present invention. Wherein the mammal is directed to ingest one or more of the beverage compositions, such direction may be that which instructs and/or informs the user that use of the beverage composition may and/or will provide treatment against dental erosion, dental discoloration or both. For example, such direction may be oral direction (e.g., through oral instruction from, for example, a physician, dental professional, sales professional or organization, and/or radio or television media (i.e., advertisement) or written direction (e.g., through written direction from, for example, a physician or dental professional (e.g., scripts), sales professional or organization (e.g., through, for example, marketing brochures, pamphlets, or other instructive paraphernalia), written media (e.g., internet, electronic mail, or other computer-related media), and/or packaging associated with the beverage composition (e.g., a label present on a package containing the beverage composition). As used herein, "written" means through words, pictures, symbols, and/or other visible descriptors. Such descriptors need not utilize the actual words "dental", "discoloration" and/or "erosion", but rather use of words, pictures, symbols, and the like conveying the same or similar meaning are contemplated within the scope of this invention.

According to the present invention, the mammal ingests or is directed to ingest one or more of the compositions as described herein. Such ingestion or direction is typically at least once monthly, more typically at least once weekly, and most preferably at least once daily. Preferably, such ingestion or direction is in place of erosive beverage compositions, for example, low pH beverage compositions or carbonated beverages which do not comprise a polyphosphate compound as described herein. Additionally, optimum treatment against dental health problems will typically further involve standard dental care, including using standard dentifrices according to standard methods, e.g., using toothpastes and/or oral rinses which are intended for prophylaxis of common dental problems such as dental caries and the like.

As stated, the present method relates to treating dental erosion, dental discoloration or both comprising orally administering to a mammal (preferably, a human) a beverage composition having a pH of greater than about 5.5; wherein the beverage composition comprises a polyphosphate compound having the structure:

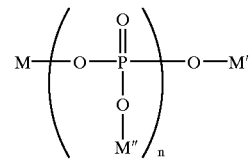

wherein n is an integer averaging from about 7 to about 100 and M, M', and M" are each, independently, selected from the group consisting of sodium and potassium.

Preferably, the present beverage compositions comprise from about 0.001% to about 0.5%, more preferably from about 0.03% to about 0.3%, even more preferably from about 0.05% to about 0.2%, and most preferably from about 0.05% to about 0.1% of the compound, by weight of the beverage composition.

Also preferably, n is an integer averaging from about 10 to about 30, more preferably averaging from about 13 to about 25, and most preferably averaging from about 19 to about 25. Most preferably, n is an integer averaging about 21.

Also preferably, each of M, M', and M" are sodium.

The present beverage compositions herein have a pH of greater than about 5.5, preferably from about 6.0 to about 9.5, and most preferably from about 6.5 to about 8.0. Beverage composition acidity can be adjusted to and maintained within the requisite range by known and conventional methods, e.g., the use of food grade buffers. The component utilized to adjust and maintain the appropriate pH is not critical to the present invention.

The beverages used in the present methods provide protection against dental discoloration caused by coffee, tea, wine, and other beverages with tooth staining potential, tobacco use, antimicrobial agents, and mixtures thereof. Moreover, the treatment provides protection against dental erosion, dental discoloration or both for up to about four hours, preferably at least about 3.5 hours, and even more preferably at least about three hours. While not wanting to be bound by any one theory, it is believed that the polyphosphate compositions of the present invention adhere to the pellicle on the tooth enamel, strengthening it, and protecting the enamel from a later attack by an acidic beverage.

It has been further excitingly discovered that treatment of dental erosion, dental discoloration or both is provided herein through use of the beverage composition even wherein the beverage composition is substantially free of components which are often associated with treatment of dental erosion, dental discoloration or both, i.e., fluoride and/or calcium. The present inventors have further discovered that such treatment is also provided even wherein the beverage composition is substantially free of phosphate derived from compounds other than the polyphosphate compound defined herein. Accordingly, a preferred but not requisite embodiment herein are beverage compositions which are substantially free of fluoride, calcium, and/or phosphate derived from one or more compounds other than the polyphosphate compound defined herein. As used herein, "substantially free of fluoride" or the like means that the composition comprises less than about 0.1% of fluoride (as an element, including in ionic form), preferably less than about 0.075% of fluoride, more preferably less than about 0.05% of fluoride, and most preferably less than about 0.025% of fluoride, all by weight of the beverage composition. As used herein, "substantially free of calcium" or the like means that the composition comprises less than about 0.1% of calcium (as an element, including in ionic form), preferably less than about 0.075% of calcium, more preferably less than about 0.05% of calcium, and most preferably less than about 0.025% of calcium, all by weight of the beverage composition. As used herein, "substantially free of a phosphate derived from one or more compounds other than the polyphosphate compound defined herein" or the like means that the composition comprises less than about 0.1% of such other phosphate (as an element, including in ionic form), preferably less than about 0.075% of such other phosphate, more preferably less than about 0.05% of such other phosphate, and most preferably less than about 0.025% of such other phosphate, all by weight of the beverage composition.

In accordance with the present method it is further surprising that one or more sweeteners may be included in the beverage compositions with maintenance of treatment of dental erosion, dental discoloration or both. Such sweeteners are described herein below as an optional component of the beverage composition.

Kits of the Present Invention

The present invention further relates to kits comprising a beverage composition as described herein and information that use of the beverage composition provides treatment against dental erosion, dental discoloration or both. For example, such information may be oral information disseminated as part of the kit, but is preferably written information, typically present on packaging associated with the beverage composition (e.g., a label present on a package containing the beverage composition or package insert included within the kit). As used herein, "written" means through words, pictures, symbols, and/or other visible information. Such information need not utilize the actual words "dental", "discoloration" and/or "erosion", but rather use of words, pictures, symbols, and the like conveying the same or similar meaning are contemplated within the scope of this invention. Such information may also include information about general dental health and reasons for which dental health, and particularly treatment against dental erosion, is important for the user.

Optional Components of the Beverage Compositions Utilized in the Present Kits and Methods The compositions utilized in the kits and methods of the present invention may comprise additional optional components to enhance, for example, their stability, organoleptic properties and/or nutritional profile. For example, water, beverage emulsions, thickeners, sweeteners, coloring agents, nutrients, carbonation components, soluble fibers, preservatives, and the like may be included in the compositions herein. Such optional components may be dispersed, solubilized, or otherwise mixed into the present compositions. These components may be added to the compositions herein provided they do not substantially hinder the properties of the beverage composition. Non-limiting examples of optional components suitable for use herein are given below.

Water

Since the present compositions are beverage compositions, water is typically utilized in the methods and kits of the present invention. As used herein, the term "water" includes the total amount of water present in the composition. Accordingly, "water" includes water from flavor agents, sugar syrups, and other sources, e.g., gum solutions. Water of hydration of any solids present in the compositions is also included. Wherein water is included, water is included at levels from about 0.1% to about 99.999%, preferably from about 5% to about 99%, still preferably from about 50% to about 99%, more preferably from about 70% to about 95%, and most preferably from about 85% to about 93%, by weight of the product.

One of ordinary skill will recognize that the compounds utilized herein may also have activity as a preservative when utilized in beverage compositions, it is often preferred to utilize compositions which are also optimized for preservative activity. Therefore, as one will further understand based on recent disclosures, the water hardness may be adjusted for optimum preservative activity of the compound used herein. The term "hardness" with respect to the water herein generally refers to the presence of certain cations in water. For purposes of the present invention, hardness of the added water component is calculated according to the Association of Official Analytical Chemists (AOAC) standards set forth in Official Methods of Analysis, published by the AOAC, Arlington, Va., pp. 627–628 (14$^{th}$ Ed., 1984). Under AOAC standards, hardness is the sum of $CaCO_3$ equivalents (mg/L) in water, which sum is obtained by multiplying the concentrations (mg/L) found of the following cations in the water by the factors (see Table 1, below).

TABLE 1

| Cation | Factor |
|--------|--------|
| Ca | 2.497 |
| Mg | 4.116 |
| Sr | 1.142 |
| Fe | 1.792 |
| Al | 5.564 |
| Zn | 1.531 |
| Mn | 1.822 |

Compounds which impart hardness to water are primarily magnesium and calcium carbonates, bicarbonates, sulfates, chlorides, and nitrates, although other compounds which can contribute polyvalent cations to water can also impart hardness. Water based on hardness is normally classified as soft (0–60 ppm water hardness), moderately hard (61–120 ppm water hardness), and very hard (over 180 ppm). It is preferred herein that the compositions have a water hardness of about 0 ppm to about 120 ppm, more preferably from about 0 ppm to about 60 ppm, and most preferably from about 0 ppm to about 30 ppm. As it is especially preferred, for example, that the compositions herein are substantially free of calcium, such preference for relatively low water hardness (moderately hard or soft) is consistent with the present invention.

Excessively hard water may be treated or softened by known and conventional methods to reduce hardness to appropriate levels. Accordingly, wherein water is treated, this treated water can then be used as the added water component of the beverage product.

Beverage Emulsions

Beverage compositions utilized herein may optionally, but preferably, comprise from about 0.2% to about 5%, preferably from about 0.5% to about 3%, and most preferably from about 0.8% to about 2%, of a beverage emulsion. This beverage emulsion can be either a cloud emulsion or a flavor emulsion.

For cloud emulsions, the clouding agent can comprise one or more fats or oils stabilized as an oil-in-water emulsion using a suitable food grade emulsifier. Any of a variety of fats or oils may be employed as the clouding agent, provided that the fat or oil is suitable for use in foods and/or beverages. Preferred are those fats and oils that have been refined, bleached and deodorized to remove off-flavors. Especially suitable for use as clouding agents are those fats that are organoleptically neutral. These include fats from the following sources: vegetable fats such as soybean, corn, safflower, sunflower, cottonseed, canola, and rapeseed; nut fats such as coconut, palm, and palm kernel; and synthetic fats. See e.g., Kupper et al., U.S. Pat. No. 4,705,691, issued Nov. 10, 1987, for suitable fat or oil clouding agents.

Any suitable food grade emulsifier can be used that can stabilize the fat or oil clouding agent as an oil-in-water emulsion. Suitable emulsifiers include gum acacia, modified food starches (e.g., alkenylsuccinate modified food starches), anionic polymers derived from cellulose (e.g., carboxymethylcellulose), gum ghatti, modified gum ghatti, xanthan gum, tragacanth gum, guar gum, locust bean gum, pectin, and mixtures thereof. See e.g., Kupper et al., U.S. Pat. No. 4,705,691, issued Nov. 10, 1987. Modified starches treated to contain hydrophobic as well as hydrophilic groups, such as those described in Caldwell et al., U.S. Pat. No. 2,661,349, are preferred emulsifiers for use as herein. Octenyl succinate (OCS) modified starches such as those described in Marotta et al., U.S. Pat. No. 3,455,838 and Barndt et al., U.S. Pat. No. 4,460,617 are especially preferred emulsifiers.

Flavor emulsions useful in beverage products of the present invention comprise one or more suitable flavor oils, extracts, oleoresins, essential oils and the like, known in the art for use as flavorants in beverages. This component can also comprise flavor concentrates such as those derived from concentration of natural products such as fruits. Terpeneless citrus oils and essences can also be used herein. Examples of suitable flavors include, for example, fruit flavors such as orange, lemon, lime and the like, cola flavors, tea flavors, coffee flavors, chocolate flavors, dairy flavors. These flavors can be derived from natural sources such as essential oils and extracts, or can be synthetically prepared. The flavor emulsion typically comprises a blend of various flavors and can be employed in the form of an emulsion, alcoholic extract, or spray dried. The flavor emulsion can also include clouding agents, with or without weighting agents, as previously described. See e.g., Kupper et al., U.S. Pat. No. 4,705,691, issued Nov. 10, 1987.

Flavor emulsions are typically prepared by mixing one or more flavoring oils (from about 0.001% to about 20%) with an emulsifying agent (from about 1% to about 30%) and water. Emulsions of particles with diameters of from about 0.1 to about 3.0 microns are suitable. Preferably, the particles are about 2.0 microns or less in diameter. Most preferably, the particles are about 1.0 microns or less in diameter. The emulsifying agent coats the particularized flavor oil to aid in preventing coalescence and in maintaining an appropriate dispersion. The viscosity and specific gravity of the flavor emulsion are regulated to be compatible with the finished beverage. See e.g., Kupper et al., U.S. Pat. No. 4,705,691, issued Nov. 10, 1987.

Flavor Agents

The beverage compositions utilized herein may comprise one or more flavor agents selected from fruit juice, tea solids, milk solids, fruit flavors, botanical flavors, and mixtures thereof. When fruit juice is included, the beverages of the present invention can comprise from about 0.1% to about 40%, preferably from about 1% to about 20%, more preferably from about 2% to about 10%, and most preferably from about 3% to about 6%, fruit juice. (As measured herein, the weight percentage of fruit juice is based on a single strength 2° to 16° Brix fruit juice). It is understood, however, that many fruit juices contribute to the acidity of the beverage. As such, certain fruit juices should be used in lower concentrations or neutralized so as to raise the pH of the resulting beverage. Those skilled in the art will understand the difference between the acidity resulting from different fruit juices and how to neutralize any excessive acidity. The fruit juice can be incorporated into the beverage as a puree, comminute, or as a single strength or concentrated juice. Especially preferred is incorporation of the fruit juice as a concentrate with a solids content (primarily as sugar solids) of from about 20° to about 80° Brix.

The fruit juice can be any citrus juice, non-citrus juice, or mixture thereof, which are known for use in dilute juice beverages. The juice can be derived from, for example, apple, cranberry, pear, peach, plum, apricot, nectarine, grape, cherry, currant, raspberry, gooseberry, elderberry, blackberry, blueberry, strawberry, lemon, lime, mandarin, orange, grapefruit, cupuacu, potato, tomato, lettuce, celery, spinach, cabbage, watercress, dandelion, rhubarb, carrot, beet, cucumber, pineapple, coconut, pomegranate, kiwi, mango, papaya, banana, watermelon, passion fruit, tangerine, and cantaloupe. Preferred juices are derived from apple, pear, lemon, lime, mandarin, grapefruit, cranberry, orange, strawberry, tangerine, grape, kiwi, pineapple, passion fruit, mango, guava, raspberry and cherry. Citrus juices, preferably grapefruit, orange, lemon, lime, and mandarin juices, as well as juices derived from mango, apple, passion fruit, and guava, as well as mixtures of these juices are most preferred.

Fruit flavors may also be utilized. As described above with respect to flavor emulsions, fruit flavors may be derived from natural sources such as essential oil and extracts, or can be synthetically prepared. Fruit flavors may be derived from fruits through processing, particularly concentrating. Wherein fruit juices are concentrated or evaporated, the water which is removed or the condensate contains volatile substances which comprise the flavor of the fruit. Often, such flavor is added to a juice concentrate to enhance the flavor thereof. The condensate may also be used to flavor "near waters" (lightly flavored water).

Botanical flavors may also be utilized. As used herein, the term "botanical flavor" refers to a flavor derived from parts of a plant other than the fruit; i.e., derived from nuts, bark, roots, and/or leaves. Also included within the term "botanical flavor" are synthetically prepared flavors made to simulate botanical flavors derived from natural sources. Botanical flavors can be derived from natural sources such as essential oils and extracts, or can be synthetically prepared. Suitable botanical flavors include jamaica, kola, marigold, chrysanthemum, chamomile, ginger, valerian, yohimbe, hops, eriodictyon, ginseng, bilberry, rice, red wine, mango, peony, lemon balm, nut gall, oak chip, lavender, walnut, gentiam, luo han guo, cinnamon, angelica, aloe, agrimony, yarrow and mixtures thereof.

Tannic acid or other similar acids can be used to provide an astringent taste to the beverage. From about 0.001% to about 10% tannic acid is used. Other flavor enhancers, as well as flavorants such as chocolate and vanilla can also be used.

Wherein tea solids are included, the beverages of the present invention can comprise from about 0.01% to about 1.2%, preferably from about 0.05% to about 0.8%, by weight of the beverage product, of tea solids. The term "tea solids" as used herein means solids extracted from tea materials including those materials obtained from the genus *Camellia* including *C. sinensis* and *C. assaimica*, for instance, freshly gathered tea leaves, fresh green tea leaves that are dried immediately after gathering, fresh green tea leaves that have been heat treated before drying to inactivate any enzymes present, unfermented tea, instant green tea, and partially fermented tea leaves. Green tea materials are tea leaves, tea plant stems, and other plant materials that are related and which have not undergone substantial fermentation to create black teas. Members of the genus *Phyllanthus, Catechu gambir* and Uncaria family of tea plants can also be used. Mixtures of unfermented and partially fermented teas can be used.

Tea solids for use in beverages of the present invention can be obtained by known and conventional tea solid extraction methods. A particularly preferred source of green tea solids can be obtained by the method described in Ekanayake et al., now U.S. Pat. application 6,063,428 U.S. application Ser. No. 08/606,907, now U.S. Pat. No. 6,063,428 filed Feb. 26, 1996. Tea solids so obtained will typically comprise caffeine, theobromine, proteins, amino acids, minerals and carbohydrates. Suitable beverages containing tea solids can be formulated according to Tsai et al., U.S. Pat. No. 4,946,701, issued Aug. 7, 1990. See also, Ekanayake et al., U.S. Pat. No. 5,427,806, issued Jun. 26, 1995, for a suitable sources of green tea solids for use in the present invention.

Beverage compositions utilized herein may also comprise milk solids. These milk solids can be derived from various sources including whole milk, skim milk, condensed milk, and dried milk powder. As used herein, the term "milk" will be used to describe an aqueous dispersion of milk solids, such as fluid (whole or skim milk) or non-fat dry milk or condensed milk diluted with water. The amount of milk included typically ranges from about 5% to about 99.8%, preferably from about 5% to about 75%, more preferably from about 5% to about 40%, and most preferably from about 5% to about 15%. The amount of non-fat milk solids correlating to these levels of milk solids is in the range of from about 0.5% to about 8.2%, from about 0.5% to about 6.2%, from about 0.5% to about 3.3%, and from about 0.5% to 1.2% of the beverage, respectively.

Thickeners

Beverages compositions utilized herein, especially dilute juice beverages and beverages comprising tea solids may further comprise thickeners, including xanthan gum, carboxymethylcellulose, propylene glycol alginate, gellan gum, guar gum, pectin, tragacanth gum, gum acacia, locust bean gum, gum arabic, gelatin, as well as mixtures of these thickeners. These thickeners are typically included in the beverages of the present invention at levels up to about 0.1%, depending on the particular thickener involved and the viscosity effects desired.

Sweeteners

The beverage compositions utilized herein can, and typically will, contain an effective amount of one or more sweeteners, including carbohydrate sweeteners and natural and/or artificial no/low calorie sweeteners. As stated herein above, it has been surprisingly discovered that inclusion of one or more sweeteners may not be deleterious to the treatment of dental erosion or discoloration when utilized in the presently described beverage compositions. The amount of the sweetener used in the beverages of the present invention typically depends upon the particular sweetener used and the sweetness intensity desired. For no/low calorie sweeteners, this amount varies depending upon the sweetness intensity of the particular sweetener.

The beverages of the present invention can be sweetened with any of the carbohydrate sweeteners, preferably monosaccharides and/or disaccharides. Sweetened beverages will typically comprise from about 0.1% to about 20%, most preferably from about 6 to about 14%, sweetener. These sugars can be incorporated into the beverages in solid or liquid form but are typically, and preferably, incorporated as a syrup, most preferably as a concentrated syrup such as high fructose corn syrup. For purposes of preparing beverages of the present invention, these sugar sweeteners can be provided to some extent by other components of the beverage such as, for example, the fruit juice component and/or flavors.

Preferred sugar sweeteners for use in beverage products of the present invention are sucrose, fructose, glucose, and mixtures thereof. Fructose can be obtained or provided as liquid fructose, high fructose corn syrup, dry fructose or fructose syrup, but is preferably provided as high fructose corn syrup. High fructose corn syrup (HFCS) is commercially available as HFCS-42, HFCS-55 and HFCS-90, which comprise 42%, 55% and 90%, respectively, by weight of the sugar solids therein, as fructose. Other naturally occurring sweeteners or their purified extracts, such as glycyrrhizin, the protein sweetener thaumatin, the juice of Luo Han Guo disclosed in, for example, Fischer et al., U. S. Pat. No. 5,433,965, issued Jul. 18, 1995, and the like can also be used in the beverages of the present invention.

Suitable no/low calorie sweeteners include saccharin, cyclamates, acesulfame K (Sunette®D), L-aspartyl-L-phenylalanine lower alkyl ester sweeteners (e.g., aspartame); L-aspartyl-D-alanine amides disclosed in Brennan et al., U.S. Pat. No. 4,411,925; L-aspartyl-D-serine amides disclosed in Brennan et al., U.S. Pat. No. 4,399,163; L-aspartyl-L-1-hydroxymethylalkaneamide sweeteners disclosed in Brand, U.S. Pat. No. 4,338,346; L-aspartyl-1-hydroxyethylalkaneamide sweeteners disclosed in Rizzi, U.S. Pat. No. 4,423,029; L-aspartyl-D-phenylglycine ester and amide sweeteners disclosed in Janusz, European Patent Application 168,112, published Jan. 15, 1986; N-[N-3,3-dimethylbutyl)-L-α-aspartyl]-L-phenylalanine 1-methyl ester sweeteners disclosed in Gerlat et al., WO 99/30576, assigned to The Nutrasweet Co., published Jun. 24, 1999; and the like and mixtures thereof. A particularly preferred low calorie sweetener is aspartame.

Coloring Agent

Small amounts of coloring agents may be utilized in the beverage compositions herein. FD&C dyes (e.g., yellow #5, blue #2, red #40) and/or FD&C lakes are preferably used. Preferred lake dyes which may be used in the present invention are the FDA-approved Lake, such as Lake red #40, yellow #6, blue #1, and the like. Additionally, a mixture of FD&C dyes or a FD&C lake dye in combination with other conventional food and food colorants may be used. Riboflavin and β-carotene may also be used. The exact amount of coloring agent used will vary, depending on the agents used and the intensity desired in the finished product. The amount can be readily determined by one skilled in the art. Generally, if utilized, the coloring agent should be present at a level of from about 0.0001% to about 0.5%, preferably from about 0.001% to about 0.1%, and most preferably from about 0.004% to about 0.1%, by weight of the product.

Nutrients

The compositions herein are optionally, but preferably, fortified with one or more nutrients, especially one or more vitamins and/or minerals. The U.S. Recommended Daily Intake (USRDI) for vitamins and minerals are defined and set forth in the Recommended Daily Dietary Allowance-Food and Nutrition Board, National Academy of Sciences-National Research Council.

Unless otherwise specified herein, wherein a given mineral is present in the composition, the composition typically comprises at least about 1%, preferably at least about 5%, more preferably from about 10% to about 200%, even more preferably from about 40% to about 150%, and most preferably from about 60% to about 125% of the USRDI of such mineral. Unless otherwise specified herein, wherein a given mineral is present in the composition, the composition comprises at least about 1%, preferably at least about 5%, more preferably from about 10% to about 200%, even more preferably from about 20% to about 150%, and most preferably from about 25% to about 120% of the USRDI of such mineral.

Non-limiting examples of such vitamins and minerals, include niacin, thiamin, folic acid, pantothenic acid, biotin, vitamin A, vitamin C, vitamin $B_2$, vitamin $B_3$, vitamin $B_6$, vitamin $B_{12}$, vitamin D, vitamin E, vitamin K, iron, zinc, copper, iodine, chromium, and molybdenum. Preferably, wherein a vitamin or mineral is utilized the vitamin or mineral is selected from niacin, thiamin, folic acid, iodine, vitamin A, vitamin C, vitamin $B_6$, vitamin $B_{12}$, vitamin D, vitamin E, iron, and zinc. Preferably, at least one vitamin is selected from vitamin C, vitamin $B_6$, vitamin $B_{12}$, vitamin E, pantothenic acid, niacin, and biotin.

Commercially available vitamin A sources may also be included in the present compositions. Vitamin A can be provided, for example, as vitamin A palmitate (retinol palmitate) and/or as beta-carotene. The vitamin A may be in the form of, for example, an oil, beadlets or encapsulated. As used herein, "vitamin A" includes, but is not limited to, vitamin A, β-carotene, retinol palmitate, and retinol acetate. Wherein vitamin A is present in the compositions herein, the product comprises at least about 1%, preferably at least about 5%, more preferably from about 10% to about 200%, even more preferably from about 15% to about 150%, and most preferably from about 20% to about 120% of the USRDI of such vitamin. Wherein vitamin A is present in the compositions herein, it is especially preferred to include about 25% of the USRDI of vitamin A. The quantity of vitamin A to be added is dependent on processing conditions and the amount of vitamin A deliver desired after storage. Preferably, wherein vitamin A is included within the present compositions, the compositions comprise from about 0.0001% to about 0.2%, more preferably from about 0.0002% to about 0.12%, also preferably from about 0.0003% to about 0.1%, even more preferably from about 0.0005% to about 0.08%, and most preferably from about 0.001% to about 0.06% of vitamin A, by weight of the product.

Commercially available sources of vitamin $B_2$ (also known as riboflavin) may be utilized in the present compositions. Wherein vitamin $B_2$ is present in the compositions herein, the product comprises at least about 1%, preferably at least about 5%, more preferably from about 5% to about 200%, even more preferably from about 10% to about 150%, and most preferably from about 10% to about 120% of the USRDI of such vitamin.

Commercially available sources of vitamin C can be used herein. Encapsulated ascorbic acid and edible salts of ascorbic acid can also be used. Wherein vitamin C is present in the compositions herein, the product comprises at least about 1%, preferably at least about 5%, more preferably from about 10% to about 200%, even more preferably from about 20% to about 150%, and most preferably from about 25% to about 120% of the USRDI of such vitamin. Preferably, wherein vitamin C is included within the present compositions, the compositions comprise from about 0.005% to about 0.2%, more preferably from about 0.01% to about 0.12%, also preferably from about 0.02% to about 0.1%, even more preferably from about 0.02% to about 0.08%, and most preferably from about 0.03% to about 0.06% of vitamin C, by weight of the product.

Commercial sources of iodine, preferably as an encapsulated iodine may be utilized herein. Other sources of iodine include iodine-containing salts, e.g., sodium iodide, potassium iodide, potassium iodate, sodium iodate, or mixtures thereof. These salts may be encapsulated.

Nutritionally supplemental amounts of other vitamins which may be incorporated herein include, but are not limited to, vitamins $B_6$ and $B_{12}$ folic acid, niacin, pantothenic acid, folic acid, vitamin D, and vitamin E. Wherein the product comprises one of these vitamins, the product preferably comprises at least 5%, preferably at least 25%, and most preferably at least 35% of the USRDI for such vitamin.

Minerals which may optionally be included in the compositions herein are, for example, magnesium, zinc, iodine, iron, and copper. Any soluble salt of these minerals suitable for inclusion edible compositions can be used, for example, magnesium citrate, magnesium gluconate, magnesium sulfate, zinc chloride, zinc sulfate, potassium iodide, copper sulfate, copper gluconate, and copper citrate.

Iron may also be utilized in the compositions and methods of the present invention. Acceptable forms of iron are well-known in the art. See e.g., Nakel et al., U.S. Pat. Nos. 4,786,510 and 4,786,518, issued Nov. 22, 1988, Ashmead et al., U.S. Pat. No. 4,863,898, issued Sep. 5, 1989; Ashmead, U.S. Pat. No. 4,830,716, issued May 16, 1989; and Ashmead, U.S. Pat. No. 4,599,152, issued Jul. 8, 1986, all of which are incorporated by reference. The amount of iron compound incorporated into the product will vary widely depending upon the level of supplementation desired in the final product and the targeted consumer. Iron fortified compositions of the present invention typically contain from about 5% to about 100%, preferably from about 15% to about 50%, and most preferably about 20% to about 40% of the USRDI for iron.

Zinc may also be utilized in the compositions and methods of the present invention. Acceptable forms of zinc are well-known in the art. Zinc fortified compositions of the present invention typically contain from about 5% to about 100%, preferably from about 15% to about 50%, and most preferably about 25% to about 45% of the USRDI for zinc. The zinc compounds which can be used in the present invention can be in any of the commonly used forms such as, e.g., zinc sulfate, zinc chloride, zinc acetate, zinc gluconate, zinc ascorbate, zinc citrate, zinc aspartate, zinc picolinate, amino acid chelated zinc, and zinc oxide. Zinc gluconate and amino acid chelated zinc are particularly preferred.

Carbonation Component

Carbon dioxide can be introduced into the water which is mixed with a beverage syrup or into the beverage composition after dilution to achieve carbonation. The carbonated beverage can be placed into a container, such as a bottle or can, and then sealed. Any conventional carbonation methodology may be utilized to make carbonated beverage products of this invention. The amount of carbon dioxide introduced into the beverage will depend upon the particular flavor system utilized and the amount of carbonation desired.

Soluble Fibers

One or more soluble fibers may also optionally be included in the compositions utilized herein. Soluble fibers which can be used singularly or in combination in all embodiments of the present invention include but are not limited to pectins, psyllium, guar gum, xanthan, alginates, gum arabic, fructo-oligosaccharides, inulin, agar, and carrageenan. These soluble fibers may also serve as stabilizing agents in the various embodiments of this invention.

Pectin and fructo-oligosaccharides are the preferred soluble fibers herein. Even more preferably, pectin and fructo-oligosaccharides are used in combination. The preferred ratio of pectin to fructo-oligosaccharide is from about 3:1 to about 1:3, by weight of the composition. The preferred pectins have a degree of esterification higher than about 65%.

The preferred fructo-oligosaccharides are a mixture of fructo-oligosaccharides composed of a chain of fructose molecules linked to a molecule of sucrose. Most preferably, they have a nystose to kestose to fructosyl-nystose ratio of about 40:50:10, by weight of the composition. Preferred fructo-oligosaccharides may be obtained by enzymatic action of fructosyltransferase on sucrose such as those which are, for example, commercially available from Beghin-Meiji Industries, Neuilly-sur-Seine, France.

Preferred pectins are obtained by hot acidic extraction from citrus peels and may be obtained, for example, from Danisco Co., Braband, Denmark.

Wherein a soluble fiber is utilized, the desired total level of soluble dietary fiber for the present compositions of the present invention is typically from about 0.01% to about 15%, preferably from about 0.1% to about 5%, and most preferably from about 0.1% to about 2%. The total amount of soluble dietary fiber includes any added soluble dietary fiber as well as any soluble dietary fiber naturally present in any other component of the present invention.

Preservatives

Optionally, one or more preservatives may additionally be utilized herein. Preferred preservatives include, for example, sorbate and benzoate. The polyphosphate compounds described herein above are also quite useful as preservatives.

Preferably, wherein a preservative other than the present polyphosphate compound is utilized herein, one or more sorbate or benzoate preservative (or mixtures thereof) is utilized. Sorbate and benzoate preservatives suitable for use in the present invention include sorbic acid, benzoic acid, and salts thereof, including (but not limited to) calcium sorbate, sodium sorbate, potassium sorbate, calcium benzoate, sodium benzoate, potassium benzoate, and mixtures thereof. Sorbate preservatives are particularly preferred. Potassium sorbate is particularly preferred for use in the present invention.

Wherein a product comprises a sorbate and/or benzoate, the compositions of the present invention preferably comprise from about 0.0005% to about 0.04% of the sorbate and/or benzoate, more preferably from about 0.001% to about 0.035% of the sorbate and/or benzoate, and most preferably from about 0.003% to about 0.03% of the sorbate and/or benzoate, by weight of the composition. Wherein the composition comprises a mixture of one or more sorbates and/or benzoates, the total concentration of such preservatives is preferably maintained within these ranges.

Analytical Methods

Beverage compositions, for example, soft drink beverages (e.g., cola beverages) and fruit juice beverages, may cause the consumer of the beverage to experience dental erosion, dental discoloration, or both. Such dental erosion and dental discoloration is caused when ingesting a beverage composition that is acidic in nature, i.e., exhibits a pH of about 5 or below. As such, it is important to measure the erosive properties (or lack thereof) of typical beverages and the beverage compositions defined herein, and this was done according to the following in vitro erosion cycling protocol.

Tooth (dentin or enamel) specimens are prepared by cutting 3 mm–4 mm cores from extracted, human teeth using a diamond core drill. The teeth, collected by local surgeons, are stored until use in a 5% Thymol solution maintained at room temperature. Specimens are mounted on lucite rods with a dental acrylic (Dura Base, Reliance Mfg. Co.) covering all sides except the surface. Course polishing with 600-grit silicon carbide-water slurry is used to remove approximately 50 microns of the outer specimen surface to ensure homogeneity among specimens. Specimens are then polished with gamma alumina (Buehler No. 3, B Gamma Micropolish Alumina) to a mirror-like finish.

Portions of the surface of each specimen are then covered with an acid resistant nail polish (placed in a mesial-distal fashion), leaving at least one uncovered strip of tooth surface exposed for treatment. Covered portions remain covered with the acid-resistant nail polish throughout the experiment, serving as the control (untreated) areas for later microradiographic analysis.

After placing specimens in groups of four, each group of specimens is placed in 20 ml of fresh, pooled human saliva for at least one hour to form an initial layer of pellicle on the specimen surfaces prior to the first day of treatment. Typical test products (Treatment A) are listed in Table 2 A along with the acidic beverage (Coca Cola®) challenge (Treatment B), though both the treatments and challenge can be modified from study to study. Other acidic beverages used in similar studies include ginger ale, grapefruit juice, orange juice, etc. Treatment consisted of exposing test specimens to 20 grams of Treatment A (prepared fresh for each treatment) for 10 minutes. After exposure to the appropriate treatment (10 minute exposure followed by brief rinsing with deionized, distilled water), specimens are exposed to the saliva bath for five minutes before immersing into the acidic beverage challenge (Treatment B) for ten minutes. Fresh beverage is used for each treatment. This series of treatments (A followed by saliva followed by B) is repeated 7 times a day for a total of five treatment days. A general protocol is presented in Table 2 B. After each treatment, each group of specimens is rinsed with deionized, distilled water and placed in approximately 20 ml of fresh, pooled human saliva until the time of the next treatment. At any time specimens are not in treatment, they are placed in 20 ml of fresh, pooled human saliva (stirred). The specimens remain in the saliva bath overnight (stirred at room temperature).

After 5 days of treatment, thin cross-sections (80–120 µm thick) of each specimen are removed for assessment using standardized transverse microradiography (TMR) techniques. The exposed, treated area of each specimen is assessed with respect to complete mineral loss (erosion). Results are presented in Table 2 C as depth (in microns) of total mineral loss from the original specimen surface using the covered (untreated) areas as anatomical reference points.

The following example compositions were evaluated for their effect on protecting the teeth against the erosive challenge of commercially available carbonated soft drink, Coca Cola®.

TABLE 2A

| Product Tested Treatment A | Acid Beverage Treatment B |
| --- | --- |
| Polyphosphate (n = 21) in water (neutral pH) | Coca Cola ® |
| Water (neutral pH) | Coca Cola ® |
| Orange Juice (acid pH) | Coca Cola ® |

TABLE 2B

| Day 1 | TIME | |
| --- | --- | --- |
| Saliva soak (night before ~12 hr) | | |
| treatment 1 | 8:00 am | |
| saliva soak | | |
| treatment 2 | 9:00 am | |
| saliva soak | | |
| treatment 3 | 10:00 am | |
| saliva soak | | |
| treatment 4 | 11:00 pm | |
| saliva soak | | Repeat for 5 days |
| treatment 5 | 1:00 pm | |
| saliva soak | | |
| treatment 6 | 2:00 pm | |
| saliva soak | | |
| treatment 7 | 3:00 pm | |
| saliva overnight | | |

TABLE 2C

| Product Tested | Depth of Complete Mineral Loss ($\mu$m) |
| --- | --- |
| Polyphosphate (n = 21) in water (neutral pH) followed by Coke ® | 4.3 |
| Water (neutral pH) followed by Coke ® | 33.4 |
| Orange Juice (acid pH) followed by Coke ® | 40.6 |

As evidenced by the data in Tables 2 A–C, the following observations are made:

(a) An aqueous beverage with neutral pH and containing a polyphosphate compound as defined herein, and having a pH of greater than about 5.5, protects tooth enamel from acidic attack substantially better than distilled water with no polyphosphate compound; and (b) The combination of a fruit juice composition not containing a polyphosphate compound as defined herein, and having a pH of less than about 5, followed by a second acidic beverage, Coke®, is more erosive than water followed by Coke®.

Methods of Making the Beverage Compositions Utilized Herein

The beverage compositions utilized herein are prepared according to methods which are standard in the art. For example, the beverage compositions used herein can be prepared by conventional methods for formulating dilute juice beverages. Such conventional methods may involve hot packing or aseptic packaging operations.

Methods for making dilute juice beverages, for example, are described in Nakel et al., U.S. Pat. No. 4,737,375. Methods for making beverage compositions are also described by Woodroof and Phillips, *Beverages: Carbonated & Noncarbonated*, AVI Publishing Co., revised ed. 1981; and by Thorner and Herzberg, *Non-Alcoholic Food Service Beverage Handbook*, AVI Publishing Co., 2$^{nd}$ Ed., 1978).

One method for preparing the beverage compositions herein involves making a beverage concentrate, adding the concentrate to a sugar syrup containing the polyphosphate compound defined herein, and then trimming the mixture with water, sugar syrup, and beverage concentrate to obtain the requisite pH and material composition. All added water used in such preparation is adjusted to the desired hardness. In such a method, the beverage concentrate may be prepared by admixing to water, for example, an acidulant or acidic buffer, vitamins, flavorants, and preservative. An oil-in-water emulsion, which provides opacity and texture to the beverage compositions, can be added to the concentrate. The sugar syrup for use in preparing the beverage compositions is separately prepared by adding sugar syrup (e.g., high fructose corn syrup) to water, then adding (for example) ascorbic acid, the polyphosphate compound, and thickening agents to the syrup. Additional preservative may be added to the resulting sugar syrup. The sugar syrup and concentrate are combined to form a beverage composition. The beverage composition can be trimmed with added water, sugar syrup, and beverage concentrate to achieve the requisite acidity and composition of the beverage composition of utilized in the present invention. It should be understood that the foregoing serves as a non-limiting example and that other methods may be utilized to prepare the beverage compositions herein. Other well known and conventional variations of the foregoing can, therefore, by utilized to prepare the beverage compositions herein.

While particular embodiments of the present invention have been illustrated and described, it will be obvious to those skilled in the art that various changes and modifications may be made without departing from the spirit and scope of the invention, and it is intended to cover in the appended claims all such modifications that are within the scope of the invention.

EXAMPLES

The following provides specific embodiments of beverage compositions (and processes for preparing them) which may be advantageously used in the methods and kits of the present invention. These specific embodiments are illustrative of the compositions used herein and are not intended to be limited.

Components for each composition are typically admixed in the order in which they appear herein. Sodium hexametaphosphate for each composition is typically admixed under high sheer mixing to insure solubility.

Example 1

| Component | Amount |
| --- | --- |
| High Fructose Corn Syrup (HFCS)-55* | 13% |
| Fruit Juice Concentrate | 0.7% |
| Potassium Sorbate | 0.065% |
| Sodium Hexametaphosphate (n = 7) | 0.1% |
| Water (Hardness <30 ppm) | quantum satis |
| PH | 5.8 |

*High Fructose Corn Syrup containing 55% fructose

The beverage composition containing the above components is ingested by a 7-year-old male human daily for a 12 week period. Prior to this period, the 7-year-old male human has average dental health relative to humans of similar age. During this period, the 7-year-old male human experiences reduced dental erosion, and reduced dental discoloration as measured by erosion and discoloration of enamel, relative to humans of similar age which ingest typical low pH beverages not comprising a polyphosphate compound as described herein.

Example 2

| Component | Amount |
|---|---|
| High Fructose Corn Syrup (HFCS)-55 | 13% |
| Tea Solids | 0.1% |
| Potassium Sorbate | 0.065% |
| Sodium Hexametaphosphate (n = 17) | 0.1% |
| Water (Hardness <30 ppm) | quantum satis |
| PH | 6.5 |

The beverage composition containing the above components is ingested by a 24-year-old human daily for a 2 week period. Prior to this period, the 24-year-old human has average dental health relative to humans of similar age. During this period, the 24-year-old human experiences reduced dental erosion, and reduced dental discoloration as measured by erosion and discoloration of enamel, relative to humans of similar age which ingest low pH cola beverages not comprising a polyphosphate compound as described herein.

Example 3

| Component | Amount |
|---|---|
| High Fructose Corn Syrup (HFCS)-55 | 14.7% |
| Fruit Flavorant | 0.15% |
| Natural Gums | 0.01% |
| Potassium Sorbate | 0.035% |
| Sodium Hexametaphosphate (n = 21) | 0.1% |
| Vitamins | 0.005% |
| Coloring Agents | 0.003% |
| Water | quantum satis |
| PH | 6.8 |

Example 4

| Component | Amount |
|---|---|
| Fruit Flavorant | 0.5% |
| Aspartame, Artificial Sweetener | 0.2% |
| Natural Gums | 0.15% |
| Carboxymethyl cellulose | 0.05% |
| Potassium Sorbate | 0.035% |
| Sodium Hexametaphosphate (n = 21) | 0.1% |
| Beta-carotene, Vitamin $B_1$, Vitamin $B_6$, and Vitamin C | based on desired nutrient level |
| Coloring Agents | 0.003% |
| Water | quantum satis |
| PH | 7.2 |

A beverage composition of either the above Example 3 or Example 4, is ingested by a 5-year-old human child daily for a 3 week period. Prior to this period, the 5-year-old human has average dental health relative to humans of similar age. During this period, the 5-year-old human experiences reduced dental erosion, and reduced dental discoloration as measured by erosion and discoloration of enamel, relative to humans of similar age who ingest similar beverages not comprising a polyphosphate compound as described herein.

What is claimed is:

1. A method of treating dental erosion, inhibiting dental discoloration or both comprising orally administering to a mammal in need thereof an effective amount of a beverage composition having a pH of greater than about 5.5; wherein the beverage composition comprises a compound having the structure:

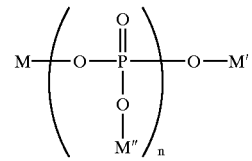

wherein n is an integer averaging from about 7 to about 100 and M, M', and M" are each, independently, selected from the group consisting of sodium and potassium.

2. A method according to claim 1 wherein the beverage composition has a pH from about 6.0 to about 9.5.

3. A method according to claim 2 wherein the beverage composition further comprises a sweetener.

4. A method according to claim 3 wherein M, M', and M" are each sodium.

5. A method according to claim 4 wherein n is an integer averaging from about 10 to about 30.

6. A method according to claim 5 wherein the beverage composition is substantially free of one or more components selected from the group consisting of calcium and fluoride.

7. A method according to claim 6 wherein n is an integer averaging from about 13 to about 25.

8. A method according to claim 7 wherein the beverage composition has a pH from about 6.5 to about 8.

9. A method according to claim 8 wherein the beverage composition comprises from about 0.1% to about 20% of the sweetener, by weight of the composition.

10. A method according to claim 9 wherein n is an integer averaging from about 19 to about 25.

11. A method according to claim 1, wherein the treatment provides protection against dental discoloration caused by coffee, tea, wine, and other beverages with tooth staining potential, tobacco use, antimicrobial agents, and mixtures thereof.

12. A method according to claim 1, wherein the treatment provides protection against dental erosion, dental discoloration or both for up to about four hours.

* * * * *